(12) United States Patent
Kluge et al.

(10) Patent No.: US 6,252,103 B1
(45) Date of Patent: *Jun. 26, 2001

(54) PREPARATION ON AN O-ALKYLISOUREA

(75) Inventors: Michael Kluge, Ludwigshafen; Knut Kessel, Mannheim; Thomas Greindl; Norbert Biedermann, both of Bad Dürkheim; Günter Scherr, Ludwigshafen; Thomas Bogenstätter, Bad Dürkheim, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/440,051

(22) Filed: Nov. 15, 1999

(30) Foreign Application Priority Data

Nov. 23, 1998 (DE) ............................................. 198 53 984

(51) Int. Cl.$^7$ ................................................... C07C 273/00
(52) U.S. Cl. ..................................................................... 558/8
(58) Field of Search ..................................................... 558/8

(56) References Cited

PUBLICATIONS

Tetrahedron by Martinkus et al vol. 30 No. 21 pp 3493–3505, Nov. 1983.*
CA:113:23916 patent IN 164490, Mar. 1989.*

J. Krechl, "Simple Amidnium Caboxylates–An Mo Treatment of Molecular Geometry and Electronic Structure" Prague Institute of Chemical Technology, vol. 54, (1989) pp. 673–683.

* cited by examiner

Primary Examiner—Jean F. Vollano
(74) Attorney, Agent, or Firm—Keil & Weinakuf

(57) ABSTRACT

A process for the preparation of an O-alkylisourea of the formula I,

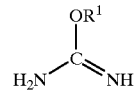

I where $R^1$ is $C_1$- to $C_{20}$-alkyl, in the form of an acid addition salt, in which urea and an alkyl-transferring reagent, if required dissolved or suspended in a diluent, are reacted at 40–200° C. in a continuously operated reactor, is described.

The diluent is preferably a recycled part-stream of the O-alkylisourea acid addition salt obtained.

5 Claims, No Drawings

PREPARATION ON AN O-ALKYLISOUREA

The present invention relates to a process for the preparation of O-alkylisoureas in the form of their acid addition salts.

O-Alkylisoureas and their acid addition salts are useful intermediates which can be reacted, for example, with primary or secondary amines to give substituted guanidinium compounds. Substituted guanidinium compounds are widespread in nature. Important members of this class of substances are, for example, amino acids, such as arginine and creatine. In addition, substituted guanidine compounds are known as sterically hindered bases, as biocides and as complex ligands. Owing to the high preparation costs, the majority of the compounds of this type are, however, greatly restricted in their industrial applicability.

One possibility for the preparation of O-alkylisoureas is the reaction of urea with alkyl-transferring reagents, such as dialkyl sulfates. The synthesis of O-methylisourea by alkylating urea with dimethyl sulfate is possible, for example, by suspending the urea in the dialkyl sulfate and heating the mixture. The reaction is strongly exothermic. A disadvantage is the poor solubility of the urea in the dialkyl sulfate. The reaction is therefore slow to start. As the reaction progresses, however, more and more urea is dissolved, which may lead to the reaction rapidly going out of control. This is a serious problem from the point of view of safety. Undesired N-alkylations and multiple alkylations are observed as a result of an uncontrolled reaction. Moreover, O-alkylisoureas undergo thermal decomposition above 100° C. The purity and the yield of the product are impaired by said circumstances.

JP 62-030983 recommends carrying out the reaction of urea and dimethyl sulfate in the presence of from 7 to 30 ml of methanol per mol of urea or dimethyl sulfate. This is said to achieve evaporative cooling, i.e. the temperature increase during the exothermic reaction is limited because some of the heat of reaction is consumed by the heat of evaporation of the methanol. However, the disadvantage of this process is that dimethyl ether is formed from methanol and dimethyl sulfate in a secondary reaction. This is undesirable owing to the danger of explosion of the dimethyl ether and the loss of alkylating agent. The formation of dimethyl ether and the vaporization of the methanol moreover lead to a considerable pressure increase and volume increase, respectively, complicating the industrial implementation of the reaction described.

It is an object of the present invention to provide an economical and easily carried out process for the preparation of O-alkylisoureas in the form of their acid addition salts, which process permits a simple reaction and leads to a particularly pure product in high yield.

We have found, surprisingly, that this object is achieved by a continuous reaction of urea with an alkyl-transferring reagent.

The present invention therefore relates to a process for the preparation of an O-alkylisourea of the formula I,

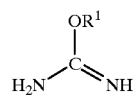

where $R^1$ is $C_1$- to $C_{20}$-alkyl, in the form of an acid addition salt, in which urea and an alkyl-tranferring reagent, if required dissolved or suspended in a diluent, are reacted at 40–200° C. in a continuously operated reactor.

The O-alkylisourea is obtained in the form of an acid addition salt by initially taking the isourea in protonated form together with an anion which originates from the alkyl-transferring reagent. The anion may be, for example, a halide, such as chloride, bromide or iodide, sulfate or a $C_1$-$C_{20}$-alkylsulfate, such as methylsulfate. The O-alkylisourea acid addition salt is obtained as a rule in the form of an oily substance. The O-alkylisourea acid addition salts often have melting points close to or below the handling temperature, or their crystallization is kinetically inhibited. If desired, the free O-alkylisourea can be isolated therefrom by conventional methods.

According to the invention, the urea and alkyl-transferring reagent are reacted at 40–200° C., preferably 60–120° C., in a continuous reactor. Suitable continuous reactors are all conventional reactor types, for example a continuous tubular reactor, a continuous stirred reactor or a continuous stirred kettle cascade.

The reaction of urea with alkyl-transferring reagents initially requires a supply of energy in order to provide the activation energy of the reaction. As soon as the reaction is initiated, the enthalpy of the exothermic reaction is liberated. On the other hand, decomposition reactions and secondary reactions become increasingly important at higher temperatures. The continuous reaction according to the invention makes it possible to overcome these problems in a surprisingly simple and elegant manner, since, in contrast to the batchwise operation, only a comparatively small amount, per unit time, of the mixture of urea and alkyl-transferring reagent is brought to the reaction temperature. The heat of reaction which is evolved in the reaction of this small amount of mixture per unit time can, on the other hand, be rapidly removed or absorbed by the diluent present. There are therefore no temporary peaks of heat quantities to be transferred, but heat flows which are essentially constant as a function of time.

The novel process is preferably carried out in a tubular reactor. The tubular reactor is a flow tube whose cross-section is small compared to the length. The shape of the cross-section, for example circular or rectangular, is not critical for the novel process. The tubular reactor is preferably operated in such a way that a narrow residence time spectrum of the reaction mixture is obtained. The individual stages of the progressing reaction occur locally in succession.

When a tubular reactor is used, energy is supplied to the entering mixture of urea and alkyl-transferring reagent, for example in a first segment of the tubular reactor, until the reaction is initiated. The mixture briefly undergoes an adiabatic temperature increase, and energy transport in the opposite direction takes place in a second segment of the tubular reactor. The tubular reactor can be thermostatted at a uniform temperature along its length. Alternatively, different temperatures can be set along the length of the tubular reactor, for example a higher temperature in the vicinity of the reactor entrance and a lower temperature in the vicinity of the reactor exit. It may sometimes be advantageous to combine an essentially adiabatically operated main reactor with an essentially isothermically operated downstream reactor.

The novel process may also be carried out using a stirred kettle cascade.

In a particularly advantageous further development of the novel process, a diluent is used for dissolving or dispersing urea and/or alkyl-transferring reagent, the diluent having a heat capacity such that the resulting heat of reaction in an essentially adiabatic reaction leads to an increase in the temperature of the reaction mixture of not more than 150° C., preferably not more than 100° C., for example not more than 80° C., in particular not more than 60° C.

Preferably, the diluent used is inert with respect to the alkyl-transferring reagent under the reaction conditions of the novel process.

Diluents having a suitable heat capacity and suitable amounts thereof for use can be readily determined by a person skilled in the art, by simple experiments or by calculations based on the known or easily determinable enthalpy of reaction for the reaction of urea with alkyl-transferring reagent. Thus, the reaction of urea with dimethyl sulfate has, for example, an enthalpy of reaction of $-53.7$ kJmol$^{-1}$. The diluent absorbs a major part of the resulting heat of reaction and thus limits the temperature increase at the start of the reaction. Decomposition reactions and secondary reactions are limited in this manner. Preferred diluents have a specific heat capacity of from 1.5 to 3 JK$^{-1}$g$^{-1}$ and are preferably used in an amount of from 0.2 to 1.0 mol per mol of reaction-limiting component. Reaction-limiting component is understood as meaning that component, i.e. urea or alkyl-transferring reagent, which is used in less than the stoichiometric amount, or any one of the components if they are used in an equimolar ratio.

It is preferable if the boiling point of the diluent used is higher than the maximum temperature of the reaction mixture during the novel process, for example higher than 200° C. This avoids the evolved heat of reaction resulting in vaporization of the diluent, which is disadvantageous owing to the formation of a multiphase mixture difficult to handle and owing to the pressure increase associated with the vaporization.

A particularly preferred diluent is an O-alkylisourea acid addition salt which is present in liquid, for example oily, form and, according to a further preferred aspect of the invention, simultaneously serves as a urea solvent.

In the novel process, the reaction temperature is 40–200° C., preferably 60–120° C. Depending on the reaction temperature, a residence time of from 5 seconds to 10 hours, preferably from 2 minutes to 1 hour, is established. It has surprisingly been found that temperatures of 140° C. or more can also be employed if a correspondingly short reaction time is chosen. In general, it is preferable if the residence time t (in minutes) and the temperature T (in K) satisfy the following equation:

$$5 \leq \int_{\tau=0}^{\tau=t/\min} 2^{\frac{T(\tau)-363K}{10K}} \cdot d\tau \leq 60$$

where $T(\tau)$ is the temperature of the reaction mixture at the time $\tau$.

At constant T, the equation simplifies to:

$$5 \leq 2^{\frac{T-363K}{10K}} \cdot \frac{\Delta t}{\min} \leq 60$$

If an average temperature in the reactor is taken for T, the total residence time $\Delta t$ in the reactor can be estimated with sufficient accuracy according to this simplified equation. This gives a residence time of from 5 to 60 minutes at 363 K (90° C.). With each temperature increase by 10 K, this residence time is halved, so that the residence time is preferably from 2.5 to 30 minutes at 373 K (100° C.) and preferably from 1.25 to 15 minutes at 383 K (110° C.).

The urea and/or the alkyl-transferring reagent can be introduced into the reactor separately or together, dissolved or suspended in a diluent. A mixture of urea and alkyl-transferring reagent, if required with the diluent, can be prepared beforehand and introduced into the reactor. For homogenization of the reaction mixture, the latter can be passed, for example, through a homogenizing apparatus, such as a static mixer. Preferred diluents are those in which urea is soluble. Dipolar aprotic solvents, such as sulfolane, can be used as solvents for urea. The concentration of urea may be 10–99, preferably 30–99, in particular 50–99, % by weight.

In a particularly preferred embodiment, the O-alkylisourea acid addition salt used according to another preferred aspect of the invention as a diluent for absorbing a part of the heat of reaction, in particular the O-alkylisourea acid addition salt obtainable by reacting the urea with the alkyl-transferring reagent used, serves as a solvent for the urea fed to the reactor. It has surprisingly been found that the O-alkylisourea acid addition salt has excellent dissolution properties for urea. The O-alkylisourea acid addition salt is moreover a suitable reaction medium for the novel reaction. For the preferred case where the O-alkylisourea acid addition salt used is the same as that prepared by the novel process, no removal of the solvent is required after the reaction. Expediently, the O-alkylisourea acid addition salt fed in for dissolving the urea is a part-stream of the O-alkylisourea acid addition salt emerging at the reactor exit. Suitable recycle ratios can easily be determined by a person skilled in the art on the basis of simple experiments. As a general guide, a recycle ratio of from 1 to 60%, preferably from 20 to 40%, may be stated. Preferably, no further solvent is used apart from the O-alkylisourea acid addition salt.

The reaction can be catalyzed, for example, by an acid, for example an organic acid, such as p-toluenesulfonic acid, methylsulfonic acid, acetic acid, chloroacetic acid or trifluoroacetic acid, or preferably a mineral acid, such as HCl, $H_2SO_4$, $HBF_4$, or $H_3PO_4$. In the case of the mineral acids, in particular mixtures, e.g. hydrochloric acid/sulfuric acid or hydrochloric acid/phosphoric acid, in a ratio of from 20:1 to 5:1, in particular from 15:1 to 8:1, may also be used. The acid can be used in an amount of from 0.01 to 1, preferably from 0.01 to 0.8, in particular from 0.01 to 0.5, equivalent, based on the urea. The O-alkylisourea acid addition salt used, as described above, according to a preferred embodiment as a diluent and solvent likewise acts as an acidic catalyst. It is generally preferable to mix the acidic catalyst with the urea before this is brought into contact with the alkyl-transferring reagent. Preferably, a catalyst other than an O-alkylisourea acid addition salt is dispensed with.

The alkyl-transferring reagent used may be a conventional alkylating agent, for example, an alkyl halide of the formula $R^1$-X, where X is halogen, in particular Cl, Br or I. Dialkyl sulfates of the formula $(R^1O)_2SO_2$ are particularly preferably used. Suitable alkyl halides and dialkyl sulfates are those in which $R^1$ may be branched or straight $C_1$–$C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Particularly preferred dialkyl sulfates are those in which $R^1$ is a linear or branched aliphatic radical of 1 to 6 carbon atoms, such as methyl, ethyl, propyl, butyl, pentyl or hexyl.

The molar ratio of urea to alkyl-transferring reagent is preferably from 3:1 to 1:2, in particular from 1.2:1 to 1:1.2.

The novel process surprisingly leads to a high selectivity of the alkylation. The selectivity of the O-alkylation is in general more than 85%, in particular more than 95%. The amount of dialkylated or polyalkylated urea is less than 2%, in general less than 1%. This is of particular importance since, during the further reaction, these products can lead to secondary reactions which may reduce the yield and purity of the secondary products.

The novel process is moreover distinguished by the fact that the urea and the alkyl-transferring reagent can be used in the form of technical-grade chemicals having a purity of, for example, about 95–98% by weight.

The O-alkylisourea acid addition salt prepared according to the invention can be reacted, without further purification, with primary or secondary amines in a second process stage to give substituted guanidine compounds. In preferred embodiments, the preparation of the O-alkylisourea acid addition salt is carried out, as described above, in the absence of a solvent and in the absence of a catalyst, so that removal of solvent or catalyst after the reaction is not necessary. The conversion of the crude product into the guanidinium salt takes place in a yield comparable with that of the reaction with pure O-alkylurea salt and leads to a product of comparable purity. A further advantage of the direct reaction of the crude O-alkylurea acid addition salt with amines is that residues of alkyl-transferring reagent which are still present in the crude product are quantitatively destroyed on contact with the amine. In the preparation of pure O-alkylurea salt, this step would have to be carried out before the further purification in a separate process step.

Aliphatic, cycloaliphatic or aromatic primary or secondary amines and aminocarboxylic acids, aminosulfonic acids and aminophosphonic acids and derivatives thereof are suitable for the reaction with the isourea derivatives of the formula I. Furthermore, primary and secondary amines which additionally contain amino or imino groups and amino-containing oligomers and polymers may also be reacted.

Preferably used amines are all the primary and secondary amines which are soluble in water or in water-miscible solvents. Preferred members among the simple amines are, inter alia, methylamine, ethylamine, n-propylamine, 2-propylamine, butylamine, isobutylamine, aniline, benzylamine and anthranilic acid. Further preferably used amino-containing compounds are, inter alia, taurine and aminocarboxylic acids, such as glycine, alanine, valine, proline, leucine, phenylalanine, lysine, methionine, cysteine, aspartic acid, iminodiacetic acid, sarcosine and their esters, amides and nitriles and their salts.

A particularly preferred amine is sarcosine, which can be used both as free acid and in particular as the Na or K salt in the form of a 5–60, preferably 35–45% strength by weight aqueous solution.

In the novel process, it is also possible to use water-soluble, amino-containing oligomers and polymers, such as alkylenediamines, dialkylenetriamines up to polyalkylenepolyamines or polyetherdiamines. Preferred members of this group are ethylenediamine, propylenediamine, butylenediamine, hexamethylenediamine, diethylenetriamine, triethylenetetramine, tetraethylenepentamine, pentaethylenehexamine, hexaethyleneheptamine and branched or linear polyalkylenepolyamines.

The use of technical-grade products in the novel process is advisable in particular where no further undesired reactive amines are admixed and it is particularly advantageous for economic reasons because, for example, the purification of the amine is expensive and complicated.

The reaction of the substituted isourea derivatives with the abovementioned amines can be carried out in water or in a water-miscible solvent or in a mixture thereof. Usually, a pH in the region of the pK of the amine is used, i.e. a pH of 6–14, preferably 8.5–12.5, particularly preferably 9.5–12.

The molar ratio of O-alkylisourea acid addition salt to primary or secondary amine is, per reactive amino group, from 2:1 to 1:2, preferably from 1.5:1 to 0.9:1. When a valuable amine is used, the O-alkylisourea acid addition salt can advantageously be used in excess.

The reaction temperatures in the second stage are from −20° C. to 100° C., preferably from 0 to 80° C., particularly preferably from 5 to 35° C.

For the reaction in the second process stage, the order of the addition of the reactants is of no particular importance. As a rule, the substituted isourea is added to the primary or secondary amine, which preferably may be present in aqueous or alcoholic solution.

The desired guanidinium derivatives are isolated in a manner known per se. As a rule, the desired product can be obtained in crystalline form by cooling the reaction solution to −20 to 60° C., in particular 0–40° C. After filtration, the purity can, if required, be improved by further recrystallization. However, it is also possible to remove the product by means of extraction from the reaction mixture in order subsequently to effect isolation cleanly by distillation or crystallization.

The example which follows illustrates the novel process.

EXAMPLE

Synthesis of O-methylisourea methylsulfate

A solution of 110 g/h of technical-grade urea in 178 g of O-methylisourea methylsulfate is metered continuously into a tubular reactor (internal diameter=0.4 cm, volume=200 cm³, jacket temperature=90° C., residence time=30 min) by means of a metering pump. 232 g/h of technical-grade dimethyl sulfate are mixed with this stream by means of a further metering pump. 520 g/h of a low-viscosity oil having an O-methylisourea methylsulfate content of 86.7% according to HPLC, corresponding to a yield of 89.8%, are obtained, 34% of which are recycled for dissolving the urea. The content of N-methyl-O-methylisourea methylsulfate is 0.53%, corresponding to a yield of 0.5%; the content of urea is 2.8%.

We claim:

1. A process for the preparation of an acid addition salt of an O-alkylisourea of the formula I

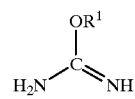

where $R^1$ is $C_1$- to $C_{20}$-alkyl, which process comprises reacting a urea feed and an alkyl-transferring reagent feed, the urea feed comprising urea dissolved in a diluent which is O-alkylisourea acid addition salt, and the alkyl transferring reagent being selected from the group consisting of alkyl halides and dialkyl sulfates, at a temperature of 40–200° C. in a continuously operated tubular reactor having a reactor entrance and a reactor exit.

2. A process as claimed in claim 1, wherein O-alkylisourea acid addition salt diluent is employed in an amount such that the heat of reaction leads to an increase in the temperature of the reaction mixture of not more than 150° C.

3. A process as claimed in claim 1, wherein the reaction mixture stays in the reactor over a residence time t and the reactor has an internal temperature T, wherein the residence time t in minutes and the temperature T in K satisfy the following equation $$5 \leq \int_{\tau=0}^{\tau=t/\min} 2^{\frac{T(\tau)-363K}{10K}} \cdot d\tau \leq 60$$

4. A process as claimed in claim 1, wherein the molar ratio of urea to alkyl-transferring reagent is from 3:1 to 1:2.

5. A process as claimed in claim 1, wherein a portion of the product acid addition salt of an O-alkylisourea of the formula I is recycled from the reactor exit to the reactor entrance.

* * * * *